United States Patent [19]

Werle et al.

[11] 4,329,519

[45] May 11, 1982

[54] PROCESS FOR THE PURIFICATION OF PENTAERYTHRITOL

[75] Inventors: Peter Werle, Gelnhausen; Gerhard Pohl, Hanau, both of Fed. Rep. of Germany

[73] Assignee: Degussa Aktiengesellschaft, Frankfurt, Fed. Rep. of Germany

[21] Appl. No.: 172,445

[22] Filed: Jul. 25, 1980

[30] Foreign Application Priority Data

Jul. 26, 1979 [DE] Fed. Rep. of Germany ....... 2930345

[51] Int. Cl.³ ...................... C07C 29/76; C07C 31/24
[52] U.S. Cl. .................................................... 568/854
[58] Field of Search ......................................... 568/854

[56] References Cited

U.S. PATENT DOCUMENTS

| | | | |
|---|---|---|---|
| 2,270,839 | 1/1942 | Wyler | 568/854 |
| 2,358,697 | 9/1944 | Filbert | 568/854 |
| 2,806,069 | 9/1957 | Cake | 568/854 |
| 2,939,887 | 6/1960 | Maury et al. | 568/853 |
| 3,968,176 | 7/1976 | Uehama et al. | 568/854 |

FOREIGN PATENT DOCUMENTS

| | | | |
|---|---|---|---|
| 684683 | 4/1964 | Canada | 568/854 |
| 713611 | 7/1965 | Canada | 568/854 |
| 799182 | 8/1958 | United Kingdom . | |

OTHER PUBLICATIONS

Ebert, "Chem. Abstracts," vol. 25 (1931), pp. 1486, 1487.

Lange, "Handbook of Chemistry," 10th ed. (1961), p. 1750.

*Primary Examiner*—Joseph E. Evans
*Attorney, Agent, or Firm*—Cushman, Darby & Cushman

[57] ABSTRACT

Crude pentaerythritol is freed from bis-pentaerythritol monoformal impurity by heating it as a dry material to a temperature of 160° to 200° C.

7 Claims, No Drawings

PROCESS FOR THE PURIFICATION OF PENTAERYTHRITOL

BACKGROUND OF THE INVENTION

The invention is directed to a process for the separation of bis pentaerythritol monoformal from crude pentaerythritol.

In the customary production of pentaerythritol by condensation of formaldehyde with acetaldehyde there is formed a crude pentaerythritol contaminated by various byproducts. A particularly disturbing product is bis pentaerythritol monoformal. The content of this byproduct generally amounts to about 2 to 5%.

It is known to remove the bis pentaerythritol monoformal from the crude pentaerythritol by treating aqueous solutions of the crude pentaerythritol at a temperature of 50° to 150° C. with a strongly acid cation exchange resin (Hercules British Pat. No. 799,182) or at a temperature of 150° to 300° C. under pressure with a cracking catalyst (Maury U.S. Pat. No. 2,939,837). These processes are expensive and therefore are little suited for use on an industrial scale.

SUMMARY OF THE INVENTION

There has now been found a process for the separation of bis pentaerythritol monoformal from crude pentaerythritol by treating it at elevated temperature wherein the crude pentaerythritol as a solid material is subjected to the treatment and there is used a temperature of about 160° to 200° C. The pentaerythritol in this way is freed to such an extent from bis pentaerythritol monoformal in a short treatment time that its content is less than 0.1%. The process requires considerably less expense than the known processes and is eminently suited for use on an industrial scale.

According to the process of the invention there can be treated pentaerythritol of any origin and it can be free of the bis pentaerythritol monoformal impurity. In the customary production by reaction of acetaldehyde with formaldehyde the pentaerythritol is obtained in aqueous solution, is separated therefrom and dried. It is advantageous for the elimination of the bis pentaerythritol monoformal impurity to further heat the pentaerythritol obtained in this way to the treatment directly after the dry.

Generally it is suitable to treat the pentaerythritol at a temperature of about 160° to 200° C. Preferably there are used temperatures of 170° to 190° C., especially 180° to 190° C. Although the pressure can be chosen at random it is advantageous to operate at normal pressure.

To carry out the process of the invention there are suited apparatuses which are customarily used for the drying of materials, for example shelf driers or drum driers.

In the treatment of the pentaerythritol according to the process of the invention generally not only is the contamination by bis pentaerythritol monoformal eliminated but simultaneously the particle size of the material tends to change so that the portion of fine particles falls and the portion of large particles correspondingly increases. From this there results for the process of the invention an additional advantage since the fine particle portion is disturbing in the further use of the pentaerythritol.

Unless otherwise indicated all parts and percentages are by weight.

The process can comprise, consist essentially of or consist of the steps set forth with the recited materials.

EXAMPLE 1

In each case there were treated 1000 grams of a crude pentaerythritol consisting of 97.0% pentaerythritol and 2.5% of bis pentaerythritol monoformal in a drum drier.

(a) The material was held for 60 minutes at 160° C. The yield was 993 grams. The gas chromatographic analysis showed a pentaerythritol content of 98.5% and a bis pentaerythritol monoformal content of below 0.1%.

(b) The material was held for 30 minutes at 170° C. The yield was 991 grams. The gas chromatographic analysis showed a pentaerythritol content of 98.7% and a bis pentaerythritol monoformal content of below 0.1%.

(c) The material was held for 30 minutes at 180° C. The yield was 991 grams. The gas chromatographic analysis showed a pentaerythritol content of 98.6%. Bis pentaerythritol monoformal was not detectable.

(d) The material was held for 15 minutes at 190° C. The yield was 990 grams. The gas chromatographic analysis showed a penterythritol content of 98.5%. Bis penterythritol monoformal was not detectable.

EXAMPLE 2

There were employed 35.0 kg of a crude pentaerythritol which contained 95.5% of pentaerythritol and 4.4% of bis pentaerythritol monoformal. The material was held for 20 minutes at 180° C. The yield was 34.5 kgrams. The gas chromatographic analysis showed a penterythritol content of 98.7%. Bis pentaerythritol monoformal was not detectable. While the pentaerythritol before the treatment contained 10% of fine particle portion below 0.1 mm particle size, this portion after the treatment was only 1%. As is apparent from the examples, the treatment time is suitably 15 to 60 minutes.

The entire disclosure of German priority application P No. 2930345.5 is hereby incorporated by reference.

What is claimed is:

1. A process for the separation of bis pentaerythritol monoformal from crude pentaerythritol containing bis pentaerythritol monoformal in an amount above 0.1% comprising subjecting the crude pentaerythritol in solid form to a temperature of 160° to 200° C. for 15 to 60 minutes until the amount of bis pentaerythritol monoformal present is reduced to below 0.1%.

2. The process of claim 1 wherein the temperature is 170° to 190° C.

3. The process of claim 2 wherein the temperature is 180° to 190° C.

4. The process of claim 1 carried out at normal pressure.

5. The process of claim 1 wherein the amount of bis pentaerythritol monoformal initially present is at least 2%.

6. The process of claim 5 wherein the amount of bis pentaerythritol monoformal initially present is between 2 and 5%.

7. The process of claim 6 wherein the amount of bis pentaerythritol monoformal initially present is 2.5 to 4.4%.

* * * * *